United States Patent [19]
Lai et al.

[11] Patent Number: 6,000,274
[45] Date of Patent: Dec. 14, 1999

[54] METHOD FOR AUTOMATICALLY DETECTING TOTAL HYDROCARBON CONTENT AND INDIVIDUAL VOLATILE ORGANIC COMPOUND CONCENTRATIONS OF WASTE GAS

[75] Inventors: Ching-Chih Lai; Hung-Chiao Cheng, both of Hsinchu; Han-Wen Chu; Hsiang-Hsien Hsiao, both of Hsinchu Hsien, all of Taiwan

[73] Assignee: Industrial Technology Research Institute, Taiwan

[21] Appl. No.: 09/012,589

[22] Filed: Jan. 23, 1998

[30] Foreign Application Priority Data

Jun. 28, 1997 [TW] Taiwan ................... 86109239

[51] Int. Cl.$^6$ ............ G01N 31/08; G01N 33/18
[52] U.S. Cl. ............ 73/23.35; 73/19.02; 73/23.38; 422/89; 210/656
[58] Field of Search ............ 73/23.35, 23.38, 73/23.41, 19.01, 19.02, 40.7; 422/89; 210/656; 96/101, 105; 95/86, 88

[56] References Cited

U.S. PATENT DOCUMENTS

| | | | |
|---|---|---|---|
| 3,447,360 | 6/1969 | Laseter | 73/23.1 |
| 3,483,731 | 12/1969 | Sanford et al. | 73/23.1 |
| 3,585,002 | 6/1971 | Boys | 23/232 |
| 3,803,384 | 4/1974 | Braunlich | 250/345 |
| 3,877,894 | 4/1975 | Swope et al. | 55/67 |
| 4,003,257 | 1/1977 | Fletcher et al. | 73/23.1 |
| 4,007,626 | 2/1977 | Roof et al. | 73/23.1 |
| 4,380,168 | 4/1983 | Ibe | 73/40.5 R |
| 4,512,897 | 4/1985 | Crowder, III et al. | 210/656 |
| 4,521,225 | 6/1985 | Jenkins et al. | 55/18 |
| 4,535,620 | 8/1985 | Cunningham | 73/23.1 |
| 4,754,136 | 6/1988 | Blakely | 250/301 |
| 4,982,052 | 1/1991 | Nolte | 585/822 |
| 5,049,509 | 9/1991 | Szakasits et al. | 436/140 |
| 5,104,810 | 4/1992 | Birbara et al. | 436/161 |
| 5,116,764 | 5/1992 | Anning et al. | 436/161 |
| 5,152,176 | 10/1992 | Bryselbout et al. | 73/23.41 |
| 5,250,093 | 10/1993 | Jiang et al. | 96/102 |
| 5,297,433 | 3/1994 | Elgas | 73/864.85 |
| 5,312,756 | 5/1994 | Jolly | 436/8 |
| 5,435,169 | 7/1995 | Mitra | 73/23.41 |
| 5,447,556 | 9/1995 | Pleil et al. | 95/87 |
| 5,492,555 | 2/1996 | Strunk et al. | 95/86 |
| 5,578,271 | 11/1996 | Simon et al. | 422/98 |
| 5,591,406 | 1/1997 | Hirai et al. | 422/80 |
| 5,637,787 | 6/1997 | Fukushima et al. | 73/23.35 |

FOREIGN PATENT DOCUMENTS 07174746  7/1995  Japan .

*Primary Examiner*—Hezron Williams
*Assistant Examiner*—J. David Wiggins
*Attorney, Agent, or Firm*—Clark & Elbing LLP

[57] ABSTRACT

A method for automatically detecting waste gas. The waste gas is led into a multiple switching valve through which the waste gas is sampled. Then, the waste gas sample is conveyed to an empty column and/or a chromatographic column, via the multiple switching valve. Then, the total hydrocarbon content of the waste gas sample is measured when the waste gas sample is conveyed to the empty column, and the waste gas sample is separated for measuring individual volatile organic compound concentrations of the waste gas sample when the waste as sample is conveyed to the chromatographic column.

6 Claims, 4 Drawing Sheets

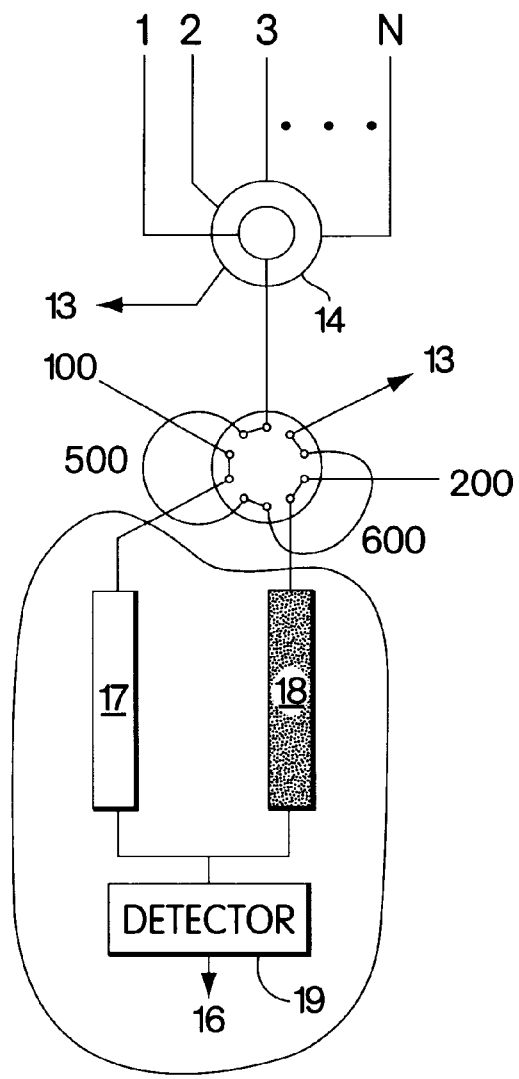
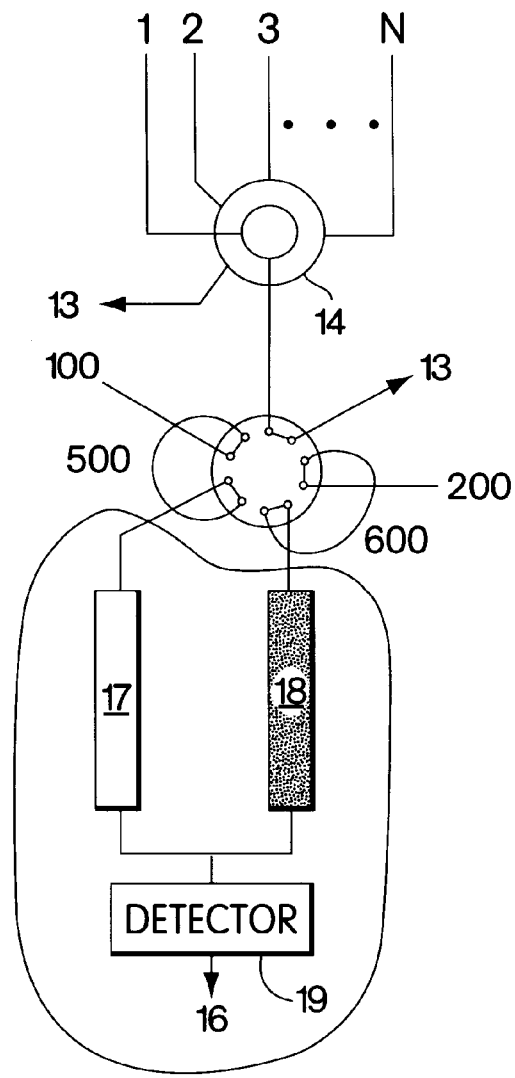
Fig. 3A
Fig. 3B

METHOD FOR AUTOMATICALLY DETECTING TOTAL HYDROCARBON CONTENT AND INDIVIDUAL VOLATILE ORGANIC COMPOUND CONCENTRATIONS OF WASTE GAS

BACKGROUND OF THE INVENTION

1. Field of the Invention

The present invention relates generally to a method for automatically detecting the total hydrocarbon content and major organic contaminant concentration of waste gas.

2. Description of the Related Art

Nowadays, environmental protection has become increasingly important. Various on-line waste-gas-detecting instruments have been widely used to monitor large-scale stationary sources of pollution such as petrochemical plants. However, none of them can simultaneously measure the total hydro-carbon (THC) content and individual volatile organic compound (VOC) concentrations in the sources of pollution.

SUMMARY OF THE INVENTION

It is therefore an object of the present invention to provide a method for automatically detecting the total hydro-carbon content and major organic contaminant concentration of waste gas to solve the above problem.

The method for automatically detecting waste gas according to the present invention is described as follows: The waste gas is led into a multiple switching valve in which the gas is sampled. Then, the waste gas sample is selectively conveyed to an empty column or a chromatographic column or both of the columns, via the multiple switching valve. Then, the total hydrocarbon content of the waste gas sample is measured when the waste gas sample is conveyed to the empty column, and the waste gas sample is separated to measure the individual volatile organic compounds concentrations of the waste gas sample when the waste gas sample is conveyed to the chromatographic column.

In this way, the total hydro-carbon (THC) content and individual volatile organic compound (VOC) concentrations of the waste gas are simultaneously measured.

BRIEF DESCRIPTION OF DRAWINGS

FIGS. 3A and 3B show the second connecting way of a ten-port switching valve of the present invention;

DETAILED DESCRIPTION OF THE PREFERRED EMBODIMENT

Figure 1:
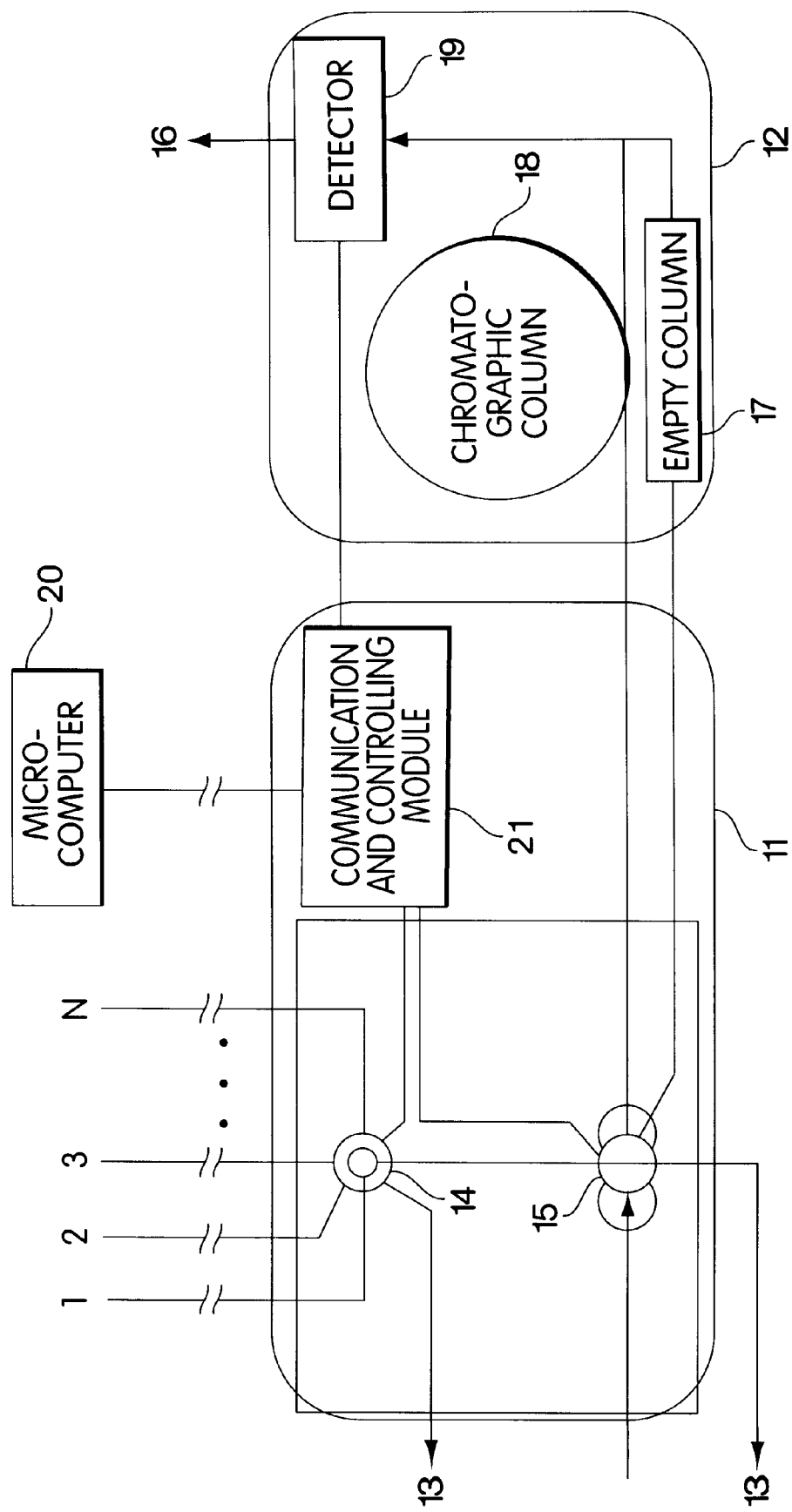
FIG. 1 is a schematic view of the waste-gas-detecting instrument of the present invention.

FIG. 1 demonstrates a method for detecting waste gas in accordance with the present invention, in which automatic sampling equipment 11 and a gas phase chromatography 12 are provided. Samples from multi-sources 1,2,3, through the operation of an air pump 13, are sequentially conveyed, through a sample conduction pipe, a stream selector 14 and a sampling valve 15, to a gas phase chromatography 12. In the gas phase chromatography 12, each sample is detected by a detector 19 to obtain its total hydrocarbon (THC) content and individual volatile organic compound (VOC) concentration. Then, the samples ark discharged through an exit 16. Moreover, a microcomputer 20 is simultaneously connected to the stream selector 14, the sampling valve 15 and the detector 19, through a communication and controlling module 21, to control the switching of the stream selector 14 and sampling valve 15 and also to record as well as analyze signals from the detector 19.

Figure 2A:
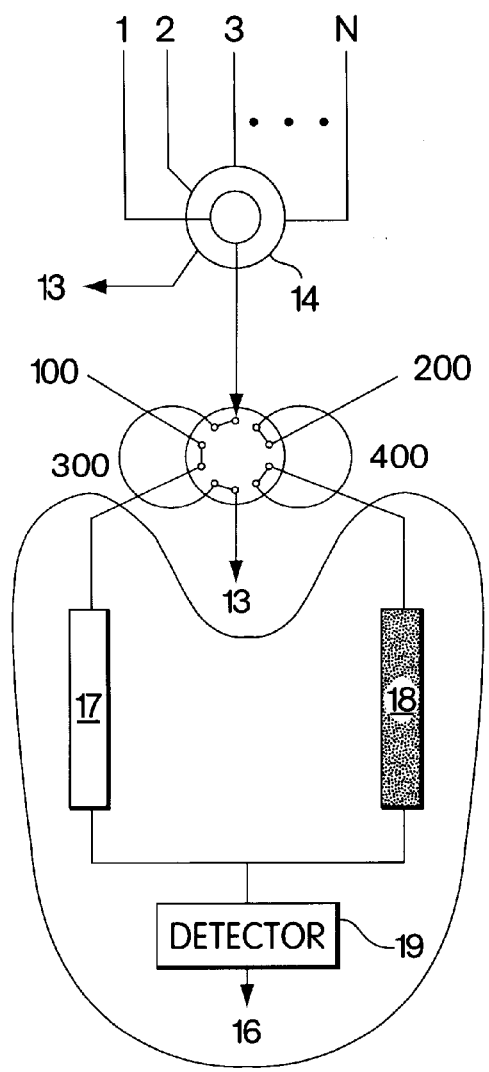
FIGS. 2A and 2B show the first connecting way of a ten-port switching valve of the present invention.
Figure 2B:
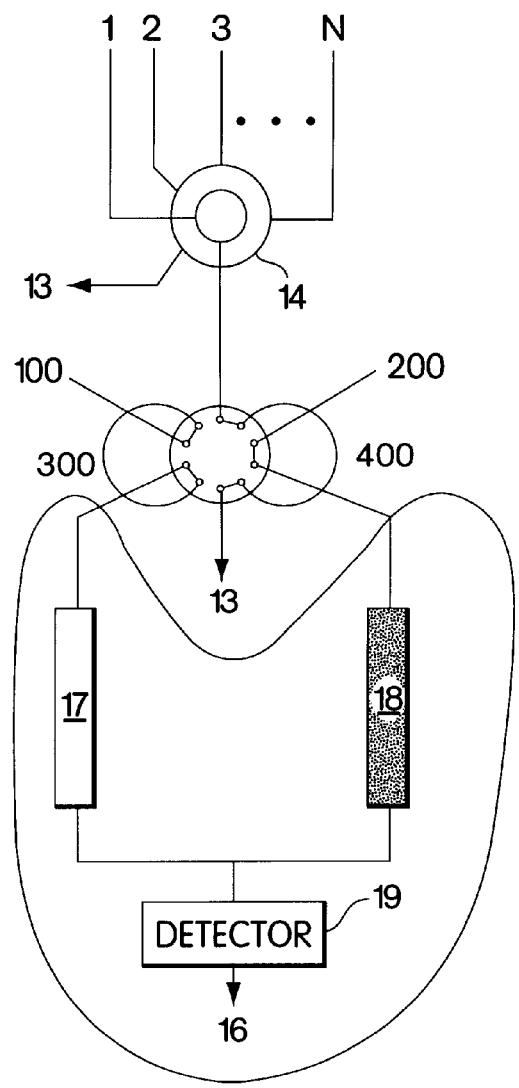

The above mentioned sampling valve can be a binary ten-port switching valve. FIGS. 2A and 2B demonstrate the first connecting way of the ten-port switching valve. Referring to FIG. 2A, a sample chosen by the stream selector 14 among the multi-sources 1,2,3 is filled in a second sample loop 300. The sample in the first sample loop 400 is driven into a chromatographic column 18 by a first carrier gas 200. In the chromatographic column 18, the sample is separated and then driven into the aforementioned detector to obtain its individual VOC concentrations. Also, a second carrier gas 100 is conveyed to an empty column 17. FIG. 2B shows the ten-port switching valve which has been switched. The sample chosen by the stream selector 14 is filled in the first sample loop 400. The sample in the second sample loop 300 is driven into the empty column 17 by the second carrier gas 100 and then conveyed to the detector in order to obtain its THC concentration.

FIGS. 3A and 3B show the second connecting way of the ten-port valve. In FIG. 3A, the sample chosen by the stream selector 14 among the multi-sources 1,2,3 is filled in sample loops 500 and 600. FIG. 3B shows the ten-port switching valve which has been switched. The sample in the second sample loop 500 is driven into the empty column 17 by the second carrier gas 100, and then conveyed to the detector in order to obtain its THC concentration. Also, the sample in the first sample loop 600 is driven into the chromatographic column 18 by the first carrier gas 200. In the chromatographic column 18, the sample is separated and then conveyed to the detector in order to measure its individual VOC concentrations.

Figure 4:
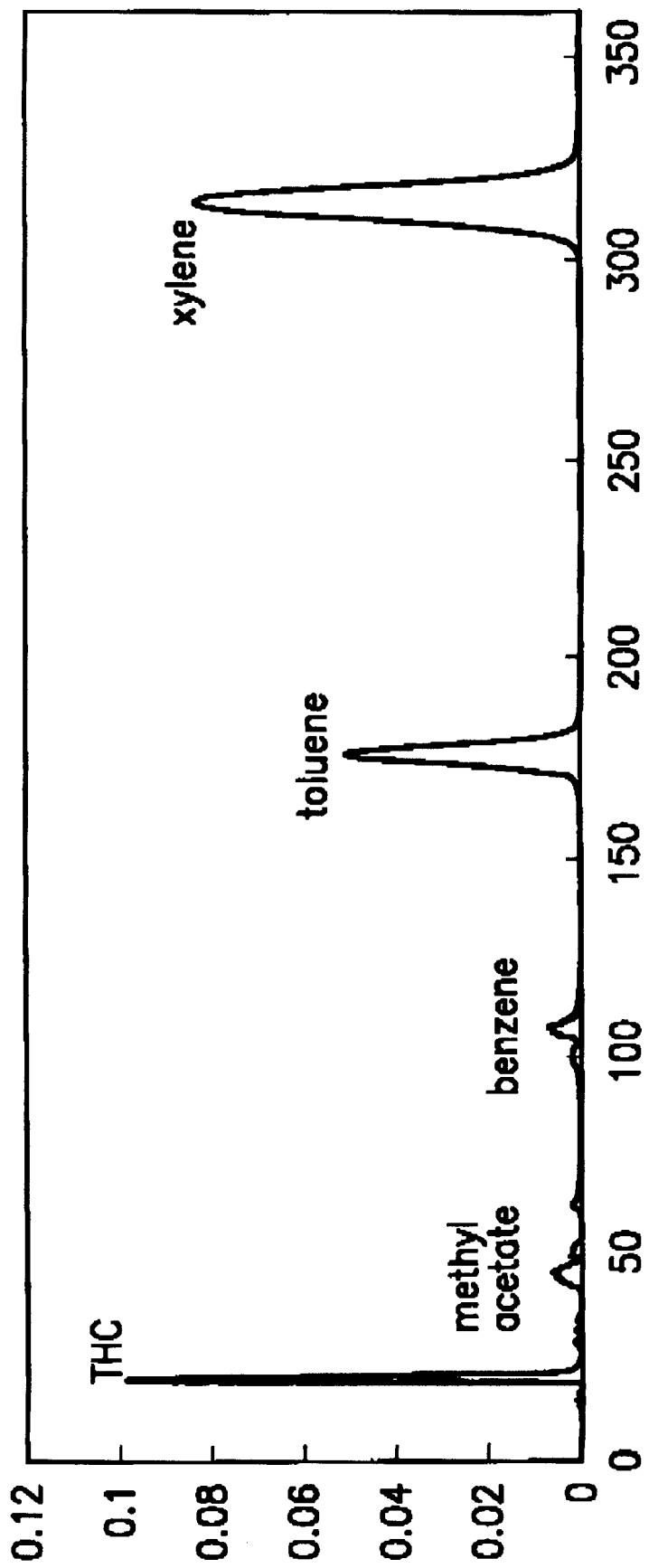
FIG. 4 demonstrate a chromatographic plot of contaminant source measurements in a petrochemical plant obtained in accordance with the methods that are the subject of the present invention.

By using the ten-port switching valve, the present invention can simultaneously or separately detect the total hydrocarbon content and the major organic contaminant concentrations of an waste gas. An example, of detecting a petrochemical plant contaminant source according to the present invention is demonstrated as follows. FIG. 4 shows a chromatography of a detected sample, wherein the horizontal axis is in the unit of seconds (time), while the vertical axis is in the unit of volts (signals). The first peak in FIG. 4 represents THC, while the other peaks respectively represent VOCs of methyl acetate, benzene, toluene and xylene. The peak values can be converted into concentration via known formulas, which will not therefore be introduced.

A molecular-sieve-filled column can be substituted for the aforementioned chromatographic column. The purpose of such a substitution is to absorb the volatile organic compounds (VOCs) except methane by the molecular sieve. Then, the methane content in the waste gas sample can be obtained.

The method for detecting waste gas of the, present invention was further analyzed for precision and accuracy as follows. The concentrations of the analyzed samples were known at the beginning. The precision was defined as the standard deviation of recovery rates of the samples which were measured at least seven times on various days. The accuracy was defined as the average of the recovery rates plus/minus twice the precision. The measurement results of the precision and accuracy of the total hydrocarbon (THC) and volatile organic compounds (VOCs) of the present invention are shown in Table 1 and Table 2. In Table 2, PGMEA is proplene glycol monomethyl ether acetate, while DMF is dimethyl Formamide. The measurement results respectively were 7.1% for THC precision, 85%–113% for THC accuracy, 6.8% for VOCs precision, and 84%–112% for VOCs accuracy. The measurement results were satisfactory.

TABLE 1

| Test Time | Tested Sample | Recovery Rate |
| --- | --- | --- |
| 1996/8/27 | 800 ppm methane | 86% |
| 1996/8/28 | 800 ppm methane | 87% |
| 1997/1/14 | 200 ppm methane | 94% |
| 1997/1/15 | 200 ppm methane | 102% |
| 1997/3/24 | 80 ppm methane | 104% |
| 1997/3/25 | 80 ppm methane | 109% |
| 1997/4/10 | 750 ppm methane | 101% |
| 1997/4/11 | 500 ppm methane | 102% |
| 1997/4/14 | 500 ppm methane | 101% |
| 1997/4/14 | 3000 ppm methane | 101% |
| 1997/4/15 | 500 ppm methane | 102% |
| Average of Recovery Rate | | 99% |
| Standard Deviation of Recovery Rate | | 7.1% |

TABLE 2

| Test Time | Tested Sample | Recovery Rate |
| --- | --- | --- |
| 1997/3/21 | 4.6 ppm n-butyl acetate | 96% |
| 1997/3/24 | 4.6 ppm n-butyl acetate | 93% |
| 1997/3/25 | 4.6 ppm n-butyl acetate | 98% |
| 1997/3/21 | 8.9 ppm PGMEA | 93% |
| 1997/3/24 | 8.9 ppm PGMEA | 90% |
| 1997/3/25 | 8.9 ppm PGMEA | 98% |
| 1997/4/11 | 137 ppm butanone | 100% |
| 1997/4/11 | 137 ppm butanone | 100% |
| 1997/4/14 | 137 ppm butanone | 109% |
| 1997/4/15 | 137 ppm butanone | 109% |
| 1997/4/10 | 159 ppm DMF | 87% |
| 1997/4/11 | 159 ppm DMF | 93% |
| 1997/4/14 | 159 ppm DMF | 107% |
| 1997/4/15 | 159 ppm DMF | 94% |
| Average of Recovery Rate | | 98% |
| Standard Deviation of Recovery Rate | | 6.8% |

While the invention has been described by way of example and in terms of the preferred embodiment, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for automatically detecting waste gas, comprising the steps of:
   (a) introducing a waste gas into a multiple switching valve, the waste gas comprised of individual volatile organic compounds (VOCs) and having a total hydrocarbon content (THC);
   (b) conveying the waste gas to an empty gas chromatographic (DC) column or a gas chromatographic column or both of the DC columns, via the multiple switching valve;
   (c) separating the individual VOCs of the waste gas in the chromatographic column; and
   (d) measuring the THC of the waste gas conveyed to the empty column and the VOC concentrations of the waste gas separated in the chromatographic column at a common detector.

2. A method for automatically detecting waste gas as claimed in claim 1, before step (a), further comprising the step of leading the waste gas into a stream selector.

3. A method for automatically detecting waste gas as claimed in claim 1, wherein the multiple switching valve is a binary ten-port switching valve.

4. A method for automatically detecting waste gas as claimed in claim 3, wherein the binary ten-port switching valve is connected to a first sample loop and a second sample loop; and in step (b), the second sample loop is filled with the waste gas which is then driven into the empty column by a first carrier gas, or the first sample loop is filled with the waste gas which is then driven into the chromatographic column by a second carrier gas.

5. A method for automatically detecting waste gas as claimed in claim 3, wherein the waste gas includes a first waste gas and a second waste gas;

between steps (a) and (b), further comprising the step of filling the first waste gas into a first sample loop which is connected to the binary ten-port switching valve, while filling the second waste gas into a second sample loop which is also connected to the binary ten-port switching valve; and in step (b), the second waste gas in the second sample loop is driven into the empty column by a first carrier gas, and the first waste gas in the first sample loop is driven into the chromatographic column by a second carrier gas.

6. A method for automatically detecting waste gas, comprising the steps of:
   (a) introducing a waste gas into a multiple switching valve, the waste gas comprised of individual volatile organic compounds (VOCs) including at least methane and having a total hydrocarbon content (THC);
   (b) conveying the waste gas to an empty gas chromatograph (DC) column or a molecular-sieve-filled DC column or both of the DC columns, via the multiple switching valve;
   (c) separating methane in the waste gas in the molecular-sieve-filled DC; and
   (d) measuring the THC of the waste gas conveyed to the empty column and the methane concentration of the waste gas separated in the molecular-sieve-filled column at a common detector.

* * * * *

UNITED STATES PATENT AND TRADEMARK OFFICE
CERTIFICATE OF CORRECTION

PATENT NO. : 6,000,274
DATED : December 14, 1999
INVENTORS : Ching-Chih Lai, Hung-Chiao Cheng, Han-Wen Chu and Hsiang-Hsien Hsiao It is certified that error appears in the above-identified patent and that said Letters Patent is hereby corrected as shown below:

Col. 2, line 5, replace "ark" with --are--;

Col. 2, line 64, delete the comma between "the" and "present";

Col. 4, line 4, replace "(DC)" with --GC--;

Col. 4, line 5, replace "DC" with --GC--;

Col. 4, line 51, replace "(DC)" with --(GC)--;

Col. 4, line 51, replace "DC" with --GC--;

Col. 4, line 52, replace "DC" with --GC--;

Col. 4, line 54, replace "DC" with --GC--;

Signed and Sealed this

Second Day of January, 2001

Attest:

*Attesting Officer*

Q. TODD DICKINSON
*Commissioner of Patents and Trademarks*